(12) United States Patent
Jafari et al.

(10) Patent No.: US 6,464,650 B2
(45) Date of Patent: Oct. 15, 2002

(54) GUIDEWIRE WITH SMOOTHLY TAPERED SEGMENT

(75) Inventors: Mo Jafari, Temecula; Sepehr Fariabi, Fremont; Lawrence E. Brennan, Temecula; Wayne E. Cornish, Oceanside; Marc M. Jalisi; David M. Anderson, both of Temecula, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/224,451

(22) Filed: Dec. 31, 1998

(65) Prior Publication Data

US 2001/0041847 A1 Nov. 15, 2001

(51) Int. Cl.[7] .................................................. A61B 5/00
(52) U.S. Cl. ...................................................... 600/585
(58) Field of Search ......................... 600/585; 604/167, 604/170, 280, 282

(56) References Cited

U.S. PATENT DOCUMENTS

| | | | | |
|---|---|---|---|---|
| 3,452,742 A | | 7/1969 | Muller | ........................... 128/2 |
| 4,003,369 A | * | 1/1977 | Heilna et al. | ................ 600/585 |
| 4,846,186 A | * | 7/1989 | Box et al. | .................... 600/585 |
| 4,854,330 A | * | 8/1989 | Evans et al. | ................. 600/585 |
| 4,867,173 A | * | 9/1989 | Leoni | .......................... 600/585 |
| 5,429,139 A | * | 7/1995 | Sauter | ......................... 600/585 |
| 5,497,783 A | | 3/1996 | Urick et al. | ................. 128/772 |

FOREIGN PATENT DOCUMENTS

| | | |
|---|---|---|
| WO | 96724978 | 7/1997 |

* cited by examiner

*Primary Examiner*—Max Hindenburg
(74) *Attorney, Agent, or Firm*—Fulwider Patton Lee & Utecht, LLP

(57) ABSTRACT

A guidewire for intraluminal advancement of a medical device within a patient which has an elongate core member with a flexible body member disposed on a distal section thereof. In one embodiment, the distal section of the elongate core member has at least one flexible segment with at least one pair of opposed tapered or parallel faces. Preferably the flexible segment with the tapered or parallel faces is disposed at the distal end of the elongate core and forms a shapable segment.

26 Claims, 3 Drawing Sheets

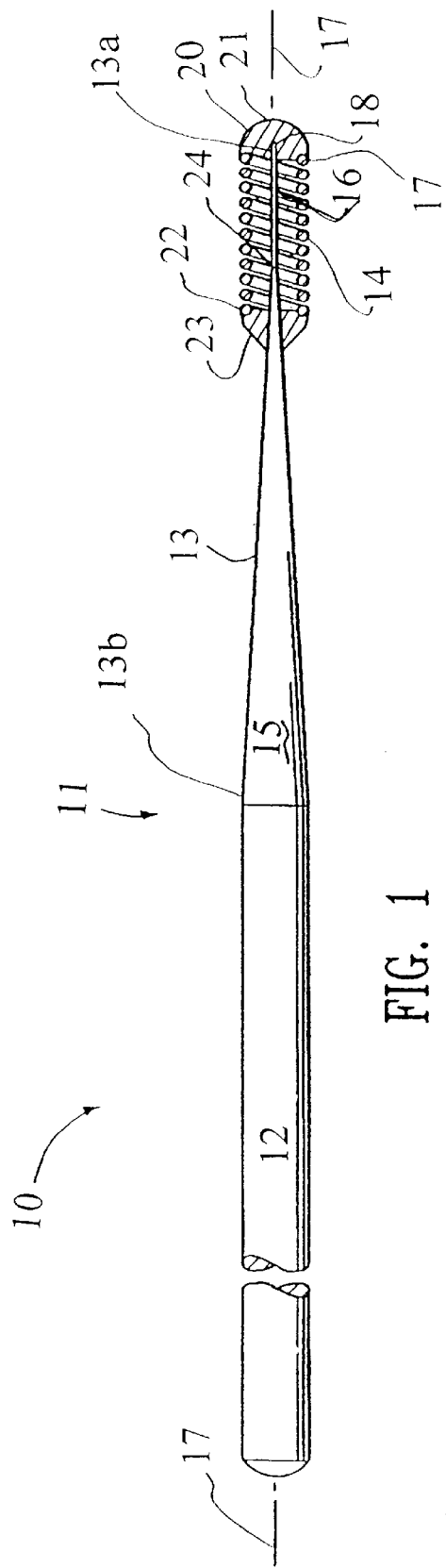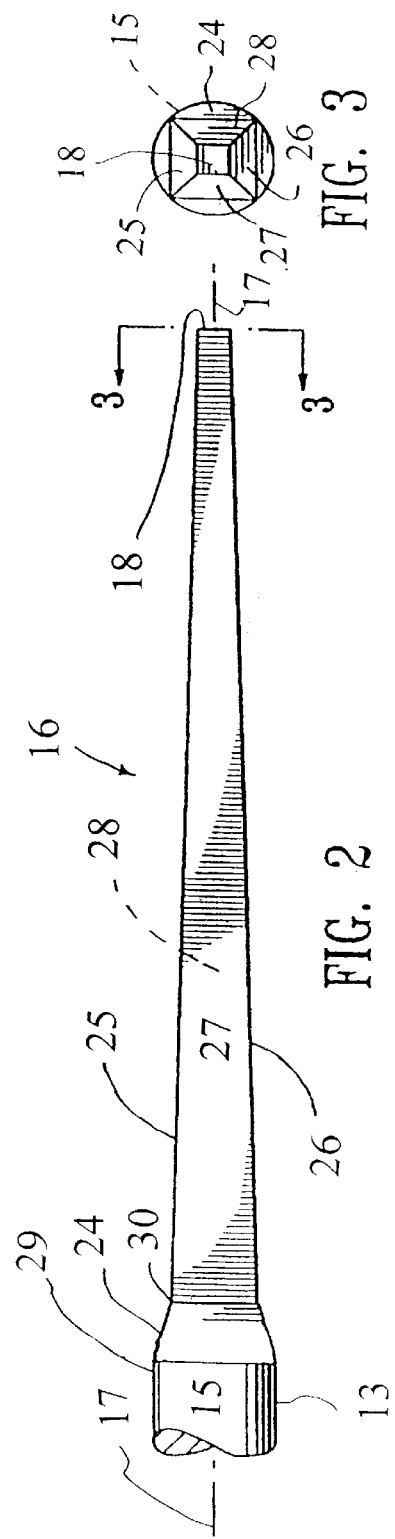

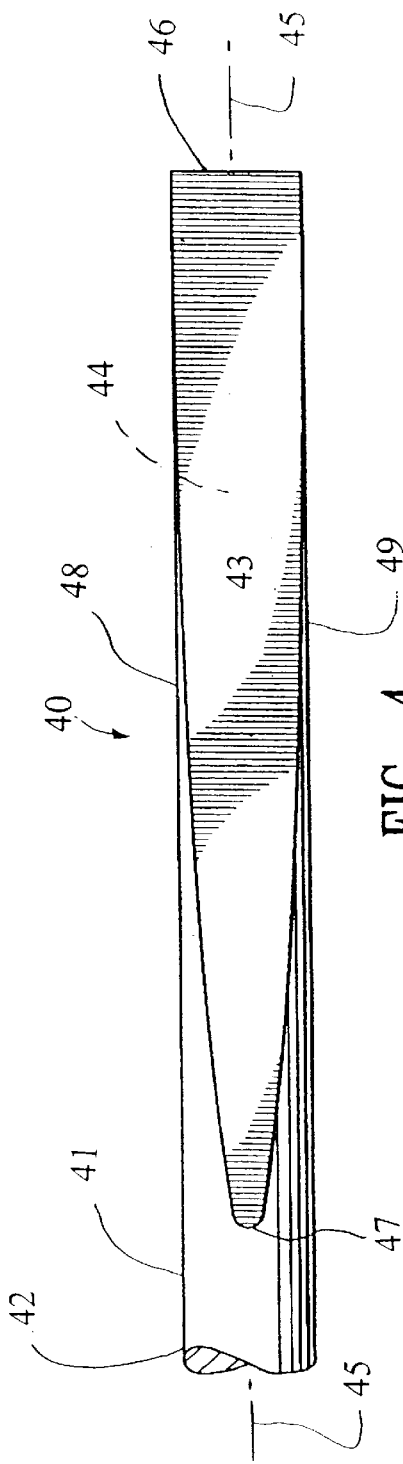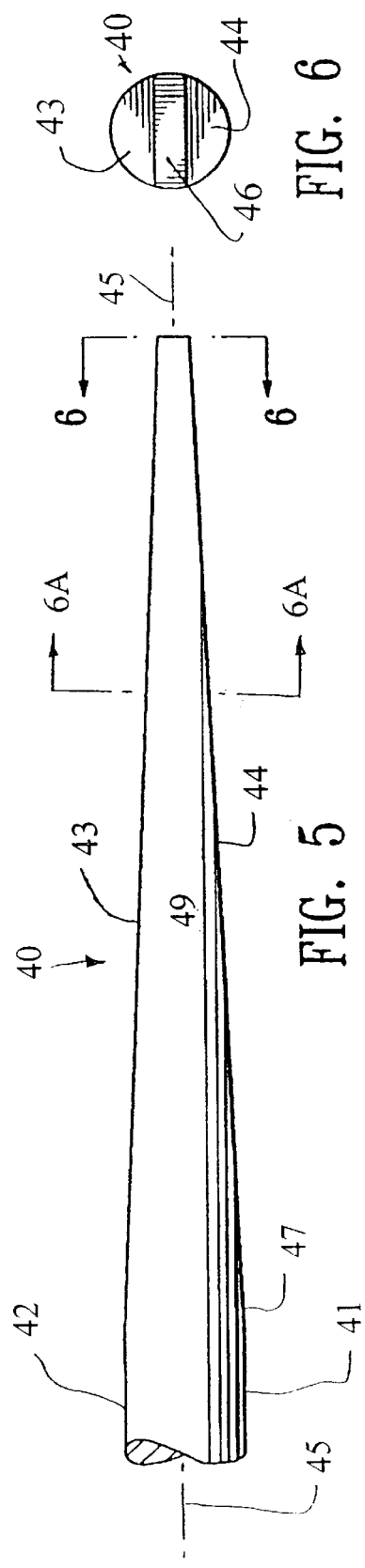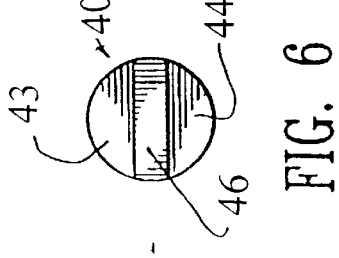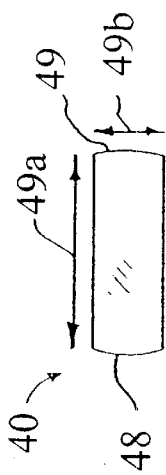

GUIDEWIRE WITH SMOOTHLY TAPERED SEGMENT

BACKGROUND OF THE INVENTION

This invention relates to the field of guidewires for advancing intraluminal devices such as stent delivery catheters, balloon dilatation catheters, atherectomy catheters and the like within body lumens.

In a typical percutaneous coronary procedure, a guiding catheter having a pre-formed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. A guidewire is first advanced by itself through the guiding catheter until the distal tip of the guidewire extends beyond the arterial location where the procedure is to be performed. Then a rail type catheter, such as described in U.S. Pat. No. 5,061,395 (Yock) and the previously discussed McInnes, et al., is mounted onto the proximal portion of the guidewire which extends out of the proximal end of the guiding catheter which is outside of the patient. The catheter is advanced over the guidewire, while the position of the guidewire is fixed, until the operative means on the rail type catheter is disposed within the arterial location where the procedure is to be performed. After the procedure the intravascular device may be withdrawn from the patient over the guidewire or the guidewire repositioned within the coronary anatomy for an additional procedure.

A guidewire may also be used in conjunction with the delivery of an intracorornary stent. One method and system involves disposing a compressed or otherwise small diameter stent about an expandable member such as a balloon on the distal end of a catheter, advancing the catheter through the patient's vascular system over a guidewire until the stent is in the desired location within a blood vessel and then expanding the expandable member on the catheter to expand the stent within the blood vessel. The dilated expandable member is then contracted and the catheter withdrawn, leaving the expanded stent within the blood vessel, holding the passageway thereof open. This latter method and system can be used concurrently with balloon angioplasty or subsequent thereto.

Further details of guidewires, and devices associated therewith for various interventional procedures can be found in U.S. Pat. No. 4,748,986 (Morrison et al.); U.S. Pat. No. 4,538,622 (Samson et al.); U.S. Pat. No. 5,135,503 (Abrams); U.S. Pat. No. 5,341,818 (Abrams et al.); and U.S. Pat. No. 5,345,945 (Hodgson, et al.) which are hereby incorporated herein in their entirety by reference thereto.

Conventional guidewires for angioplasty, stent delivery, atherectomy and other intravascular procedures usually comprise an elongate core member with one or more tapered segments near the distal end thereof. A flexible body member, such as a helical coil or a tubular body of polymeric material, is typically disposed about the distal portion of the core member. A shapable member, which may be the distal extremity of the core member or a separate shapeable ribbon which is secured to the distal extremity of the core member extends through the flexible body and is secured to the distal end of the flexible body by soldering, brazing or welding, or an adhesive in the case of polymeric flexible bodies which forms a rounded distal tip. The leading tip is highly flexible and will not damage or perforate the vessel and the portion behind the distal tip is increasingly stiff which better supports a balloon catheter or similar device.

The shapeable member or ribbon of a typical guidewire is a small diameter wire which has been flattened to a constant transverse profile. Flattening of the shapable member facilitates the shapability of the member, however, a shapable member having a constant transverse profile or flexibility can be subject to prolapse during use. Prolapse occurs when the shapable member gets bent back on itself in a constrained lumen and is difficult to straighten out with proximal manipulation. One method of preventing prolapse or reducing the occurrence thereof is to have increased stiffness at a proximal end of a shapable member. This has been done with incremental steps in the shapable member with thinner more flexible steps distally creating greater flexibility distally. However, the use of incremental steps can cause abrupt changes in flexibility of the shapable member which can be detrimental to smooth tracking and performance of the guidewire. What has been needed is a guidewire with a shapeable member at the distal section that is continuously varied in flexibility and maintains a shapeable character. The present invention satisfies these and other needs.

SUMMARY OF THE INVENTION

The present invention is directed to a guidewire having an elongate core member with a proximal section and a distal section. The distal section preferably has at least one flexible segment with two or more opposed faces that are parallel or distally tapered in essentially the same or mirror image relationship to each other. The distal section may also have one or more tapered segments which have typical distally decreasing tapers with substantially round transverse cross sections.

Preferably the flexible segment is disposed at a distal end of the distal section where it can perform the function of a shapeable member. The flexible segment has a length typically ranging from about 1 to about 12 cm, preferably about 2 to about 10 cm, although longer segments may be used. The flexible. segment provides a controlled longitudinal variation and transition in flexibility of the core segment. A flexible body member having a proximal end and a distal end is typically disposed about and attached to the distal section of the elongate core member. A flexible body member, such as a helical coil, polymer jacket, or the like, surrounds and covers at least a portion of the distal section of the elongate core member. The proximal end of the helical coil or flexible body typically is secured to the distal section of the elongate core member. Depending on the selected lengths of the helical coil and the flexible segment or shapeable member, the junction of the proximal end of the coil to the core may be at an intermediate position on the distal section or may be at an intermediate position on the flexible segment or anywhere in between.

In one preferred embodiment of a guidewire having features of the invention, the distal section of the core member has at least one flexible segment with at least two opposed tapered faces tapering distally over the length of the flexible segment to a smaller transverse separation. Optionally, the opposed tapered faces may be mirror images and parallel as well as distally tapered. In addition, the tapered faces may have either a substantially straight or curved longitudinal profile. Other than the flexible segment, the construction of the guidewire is similar to the guidewire discussed above with a flexible body member disposed about at least a portion of the distal section and is secured thereto. The proximal section of the elongate core member is nominally round in cross section and preferably with a constant diameter and said round cross section preferably extends distally to a proximal end of the flexible segment disposed on the distal section of the core. The flexible segment may be disposed anywhere on the distal section, but preferably is disposed at a distal end of the distal section, serving as a shapable member.

The taper geometry of the flexible segment may be modeled mathematically. Specific taper or face angles or contours may be selected in keeping with the principles and spirit of the invention to achieve optimum performance for specific usage requirements. These and other advantages of the invention will become more apparent from the following detailed description of the invention when taken in conjunction with the accompanying exemplary drawings.

BRIEF DESCRIPTION OF THE DRAWINGS

FIG. 1 is an elevation view, partially in section, of a guidewire embodying features of the invention.

FIG. 2 is an enlarged elevational view of a portion of the distal section of the elongated core member of the guidewire shown in FIG. 1.

FIG. 3 is an end view of the embodiment of FIG. 2, shown as viewed from line 3—3 in FIG. 2.

FIG. 4 is an elevational view of an elongated core member for a guidewire having features of the invention.

FIG. 5 is a side elevation view of the embodiment shown in FIG. 4.

FIG. 6 is a end view of the embodiment of FIGS. 4 and 5, shown as viewed from line 6—6 in FIG. 5.

FIG. 6A is a transverse cross sectional view of the flexible segment of FIG. 5 taken at lines 6A—6A.

DETAILED DESCRIPTION OF THE INVENTION

Figure 7:
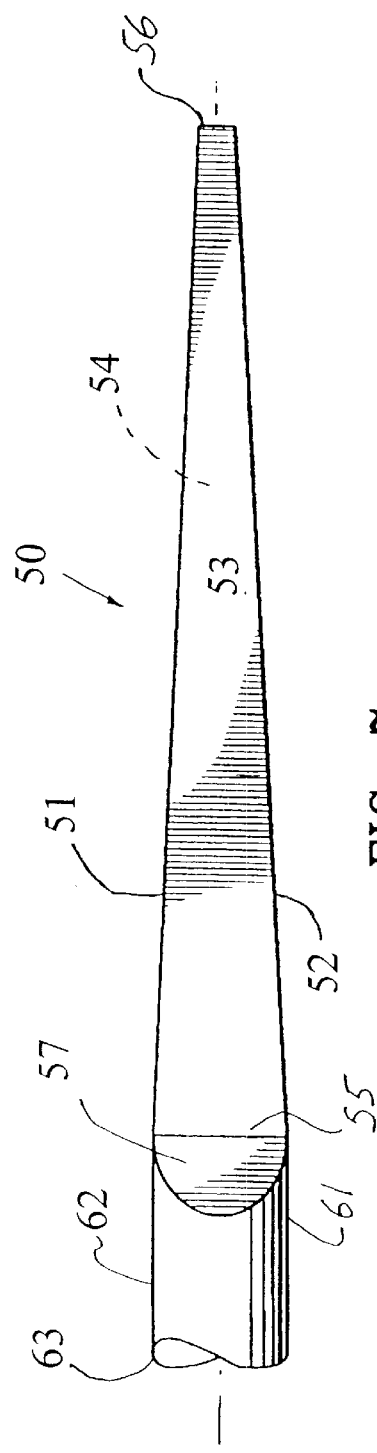
FIG. 7 is an elevational view of a portion of an elongated core member for a guidewire having features of the invention.

FIG. 1 is an elevational view of guidewire 10 which embodies features of the invention, and which includes an elongated core member 11 with a proximal core section 12, a distal core section 13, and a flexible body member 14 which is fixed to the distal core section. The distal core section 13 has a tapered segment 15, a flexible segment 16 which is distally contiguous to the tapered segment 15, a distal end 13a, and a proximal end 13b. The distal section 13 may also have more than one tapered segment 15 which have typical distally decreasing tapers with substantially round transverse cross sections. A guidewire having multiple continuous tapered segments in the distal section of the elongate core member is described in U.S. patent application Ser. No. 08/868,764, filed Jun. 4, 1997 (Cornish, et al.) entitled STEERABLE GUIDEWIRE WITH ENHANCED DISTAL SUPPORT, which is hereby incorporated by reference in its entirety.

The core member 11 may be formed of stainless steel, NiTi alloys or combinations thereof such as described in U.S. Pat. No. 5,341,818 (Abrams et al) which has been incorporated herein. Other materials such as the high strength alloys as described in U.S. Pat. No. 5,636,641 (Fariabi), entitled HIGH STRENGTH MEMBER FOR INTRACORPOREAL USE, which is incorporated herein by reference, may also be used.

The core member 11 is optionally coated with a lubricious coating such as a fluoropolymer, e.g. TEFLON® available from DuPont, which extends the length of the proximal core section. The distal section 13 is also provided with a lubricous coating, such as a MICROGLIDE™ coating used by the present assignee, Advanced Cardiovascular Systems, Inc. on many of its commercially available guidewires. Hydrophilic coatings may also be employed.

The length and diameter of guidewire 10 may be varied to suit the particular procedures in which it is to be used and the materials from which it is constructed. The length of the guidewire 10 generally ranges from about 65 cm to about 320 cm, more typically ranging from about 160 cm to about 200 cm, and preferably from about 175 cm to about 190 cm for the coronary anatomy. The guidewire diameter generally ranges from about 0.008 in. to about 0.035 in. (0.203 to 0.889 mm), more typically ranging from about 0.012 in. to about 0.018 in. (0.305 to 0.547 mm), and preferably about 0.014 in. (0.336 mm) for coronary anatomy.

The flexible segment 16 terminates in a distal end 18. Flexible body member 14, preferably a helical coil, surrounds a portion of the distal section of the elongated core 13, with a distal end 19 of the flexible body member 14 secured to the distal end 18 of the flexible segment 16 by the body of solder 20. The proximal end 22 of the flexible body member 14 is similarly bonded or secured to the distal core section 13 by a body of solder 23. Materials and structures other than solder may be used to join the flexible body 14 to the distal core section 13, and the term "solder body" includes other materials such as braze, epoxy, polymer adhesives, including cyanoacrylates and the like.

The wire from which the flexible body 14 is made generally has a transverse diameter of about 0.001 to about 0.004 inch, preferably about 0.002 to about 0.003 inch (0.05 mm). Multiple turns of the distal portion of coil may be expanded to provide additional flexibility. The helical coil may have a diameter or transverse dimension that is about the same as the proximal core section 12. The flexible body member 14 may have a length of about 2 to about 40 cm or more, preferably about 2 to about 10 cm in length. The flexible body member 14 may also be made from a polymer. Polymers suitable for forming a flexible body member 14 can include polyimide, polyethylene, polyurethane, TFE, PTFE, ePTFE and other similar materials. A flexible body member 14 in the form of a helical coil may be formed of a suitable radiopaque material such as platinum or alloys thereof or formed of other material such as stainless steel and coated with a radiopaque material such as gold.

The flexible segment 16 has a length typically ranging about 1 to about 12 cm, preferably about 2 to about 10 cm, although longer segments may be used. The form of taper of the flexible segment 16 provides a controlled longitudinal variation and transition in flexibility (or degree of stiffness) of the core segment. The flexible segment is contiguous with the core member 11 and is distally disposed on the distal section 13 so as to serve as a shapable member.

Referring to FIG. 2, the flexible segment 16 of guidewire 10 is shown in more detail. The flexible segment 16 is tapered distally both in height and width and has a generally square cross section defined by a first pair of opposed tapered faces and a second set of opposed tapered faces. The first set of opposed tapered faces consists of a top face 25 and a bottom face 26, which taper distally together to a smaller transverse separation. The second set of opposed tapered faces consists of a first side face 27 and a second side face 28 which taper distally together to a smaller transverse separation. Each of the tapered faces 25–28 are substantially axially coextensive and extend from the transition portion 24 of the distal section 13 to the distal end 18 of the flexible segment 16. Thus flexible segment 16 tapers to become progressively narrower in both transverse directions as the distal end 18 is approached. This results in a smooth decrease in cross sectional area and stiffness distally. Each of the tapered faces 25–28 has a longitudinal contour that is substantially straight. In addition, the top face 25 is a mirror image of the bottom face 26 about the longitudinal axis 17. The first side face 27 is a mirror image of the second side face 28 about the axis 17.

The short transition portion 24 is shaped to provide a generally continuous transition from the circular cross section of the distal end 29 of the tapered segment 15 to the substantially square cross section of the proximal end 30 of the flexible segment 16. Referring to FIG. 3, the first set of opposed tapered faces 25 and 26 are substantially normal at any given transverse cross section to the second set of opposed tapered faces 27 and 28. Or in other words, in any transverse cross section of the flexible segment 16, the lines representing the surfaces of the first set of opposed tapered faces 25 and 26 will be substantially normal to the lines representing the second set of opposed tapered faces 27 and 28.

The multiple tapers or faces of the flexible segment 16 may be ground simultaneously or as separate operations. A centerless grinder with profile capabilities may be used to grind the tapers or faces simultaneously. A manual centerless grinding may be employed to create separate tapers or faces in separate operations. Tapers or faces may also be formed by other means such as chemical means, e.g. etching, or laser means.

FIGS. 4, 5 and 6 depict an alternative embodiment of a flexible segment 40 wherein one pair of opposed tapered faces taper distally to a smaller transverse separation. This results in a smooth decrease in cross sectional area and stiffness distally over the length of the flexible segment 40. The flexible segment 40 is preferably integrally formed with a tapered segment 41 of a distal core section 42. The first opposed tapered face 43 and second opposed tapered face 44 slope distally and incline towards the axis 45 of the segment 40. The opposed faces 43 and 44 terminate distally at the distal end 46 of the flexible segment 40. The width of the distal end 46 can be the diameter of the proximal end 47 of the flexible segment 40. In the embodiment shown, the round cross section of the tapered segment 41 is continued in the flexible segment 40 except to the extent that the material of the core 42 has been removed or shaped in order to form the first and second opposed tapered faces 43 and 44. Thus, the side surfaces 48 and 49 of the flexible segment 40 may have a curved profile. The longitudinal contours of each of the first and second opposed tapered faces are substantially straight, in addition to being mirror images about longitudinal axis 45. In FIG. 6A a transverse cross sectional view of the flexible segment 40 taken at lines 6A—6A in FIG. 5 shows the curved profile of the side surfaces 48 and 49. In addition, the flattened shape of the cross section is indicated by the major transverse dimension 49a and the short transverse dimension 49b of the flexible segment 40. In the cross section of FIG. 6A, the major transverse dimension 49a is substantially greater than the small transverse dimension 49b.

Figure 8:
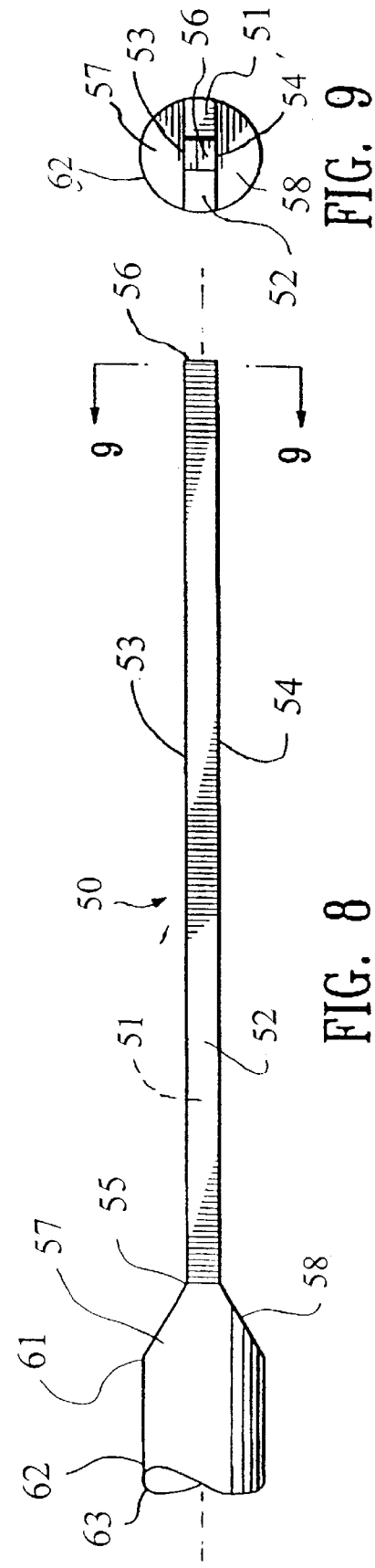
FIG. 8 is a side elevation view of the embodiment of FIG. 7.
Figure 9:
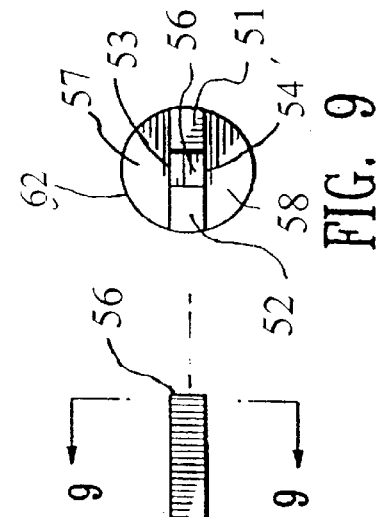
FIG. 9 is a end elevation view of the embodiment of FIGS. 7 and 8, shown as viewed from line 9—9 in FIG. 8.

FIGS. 7, 8 and 9 depict an embodiment of a flexible segment 50 with two pairs of opposed faces which are generally coextensive in an axial direction. The first pair of opposed faces consists of a first tapered face 51 and a second tapered face 52. The second pair of opposed faces consists of a first parallel face 53 and a second parallel face 54. The first tapered face 51 and second tapered face 52 taper distally to a smaller transverse separation with respect to each other such that the distance between the first tapered face 51 and the second tapered face 52 is greater at the proximal end 55 of the flexible segment 50 than at the distal end 56 of the flexible segment.

The first parallel face 53 is substantially parallel to the second parallel face 54 along the length of the flexible segment 50 except at the proximal end 55 of the flexible segment where the first and second parallel faces terminate proximally at the first transition segment 57 and a second transition segment 58. The optional first and second transition segments 57 and 58 span the difference in transverse dimension from the proximal end 55 of the flexible segment 50 to the distal end 61 of the tapered segment 62 of the distal core section 63. Although the first and second tapered faces 51 and 52 have substantially straight longitudinal contours, these contours may also be curved. The first and second transition segments 57 and 58 may also be curved so as to create a smooth transition at the proximal end 55 of the flexible segment 50.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A guidewire comprising:
   (a) an elongate core member having a proximal section and a distal section with the distal section having at least one flexible segment having a smoothly distally decreasing cross sectional area and at least a portion where a major transverse dimension is greater than a small transverse dimension; and
   (b) a flexible body member having a proximal end and a distal end which is disposed about at least a portion of the distal section of the elongate core member and wherein the distal end of the flexible body member is secured to the distal end of the distal section of the elongate core member.

2. The guidewire of claim 1 wherein the proximal section of the elongate core member has a nominally round transverse cross section and the distal section of the elongate core member further comprises a proximal end and a distal end and the flexible segment is disposed at the distal end of the distal section.

3. The guidewire of claim 2 wherein the flexible segment further comprises a pair of opposed tapered faces having longitudinal contours that are substantially straight.

4. The guidewire of claim 2 wherein the flexible segment further comprises a pair of opposed tapered faces having longitudinal contours that are curved.

5. The guidewire of claim 2 wherein the flexible segment further comprises a pair of opposed tapered faces having substantially mirror image longitudinal contours.

6. The guidewire of claim 2 wherein the flexible segment has a major transverse dimension that is substantially constant along its length.

7. A guidewire comprising:
   (a) an elongate core member having a proximal section and a distal section with the distal section having at least one flexible segment having two opposed faces, said segment tapering distally to a smaller transverse separation between said pair of faces, and said segment includes a generally rectangular cross sectional shape; and (b) said flexible segment has a major transverse dimension that is substantially constant along its length.

8. The guidewire of claim 7 wherein the proximal section of the elongate core member has a nominally round transverse cross section and the distal section of the elongate core member further comprises a proximal end and a distal end and the flexible segment is disposed at the distal end of the distal section.

9. The guidewire of claim 8 further comprising a flexible body member having a proximal end and a distal end which is disposed about at least a portion of the distal section of the elongate core member and wherein the distal end of the flexible body member is secured to the distal end of the distal section of the elongate core member.

10. The guidewire of claim 8 wherein the opposed faces have longitudinal contours that are substantially straight.

11. The guidewire of claim 8 wherein the opposed faces have longitudinal contours that are curved.

12. The guidewire of claim 8 wherein the opposed faces have substantially mirror image longitudinal contours.

13. A guidewire comprising:
   (a) an elongate core member having a proximal section and a distal section with the distal section having at least one flexible segment with a first pair of opposed tapered faces, the segment tapering distally to a smaller transverse separation between said first pair of faces, and the segment having a second set of opposed tapered faces which are axially coextensive with the first set of opposed tapered faces, the segment tapering distally to a smaller transverse separation between said second pair of faces;
   (b) a flexible body member having a proximal end and a distal end disposed about at least a portion of the distal section of the elongate core member and secured to at least a portion thereof; and
   (c) said flexible segment has at least a portion which has a cross section substantially square in shape.

14. The guidewire of claim 13 wherein the proximal section of the elongate core member has a nominally round transverse cross section and the distal section of the elongate core member further comprises a proximal end and a distal end and the flexible segment is disposed at the distal end of the distal section.

15. The guidewire of claim 14 wherein the distal end of the flexible body member is secured to the distal end of the distal section of the elongate core member.

16. The guidewire of claim 14 wherein both sets of tapered faces have a longitudinal contour that is substantially straight.

17. The guidewire of claim 14 wherein both sets of tapered faces have a longitudinal contour that is curved.

18. The guidewire of claim 14 wherein the first set of tapered faces is substantially normal to the second set of tapered faces.

19. A guidewire comprising:
   a) an elongate core member having a proximal section and a distal section with the distal section having at least one flexible segment with a first pair of opposed faces, the segment tapering distally to a smaller transverse separation between said first pair of faces, and the segment having a second set of opposed faces which are axially coextensive with the first set of opposed faces and which are substantially parallel to each other;
   b) a flexible body member having a proximal end and a distal end disposed about at least a portion of the distal section of the elongate core member and secured to at least a portion thereof.

20. The guidewire of claim 19 wherein the proximal section of the elongate core member has a nominally round transverse cross section and the distal section of the elongate core member further comprises a proximal end and a distal end and the flexible segment is disposed at the distal end of the distal section.

21. The guidewire of claim 20 wherein the distal end of the flexible body member is secured to the distal end of the distal section of the elongate core member.

22. The guidewire of claim 20 wherein the first set of opposed faces and the second set of opposed faces have a longitudinal contour that is substantially straight.

23. The guidewire of claim 20 wherein the first set of opposed faces and the second set of opposed faces have a longitudinal contour that is curved.

24. The guidewire of claim 20 wherein the second set of opposed faces have a transverse dimension greater than a transverse dimension of the first set of opposed faces along a substantial length of the flexible segment.

25. The guidewire of claim 20 wherein a transverse cross section of any portion of the flexible segment is substantially rectangular in shape.

26. The guidewire of claim 20 wherein the first set of opposed faces is substantially normal to the second set of opposed faces.

* * * * *

UNITED STATES PATENT AND TRADEMARK OFFICE
CERTIFICATE OF CORRECTION

PATENT NO. : 6,464,650 B2
DATED : October 15, 2002
INVENTOR(S) : Mo Jafari et al.

It is certified that error appears in the above-identified patent and that said Letters Patent is hereby corrected as shown below:

<u>Title page,</u>
Item [56], FOREIGN PATENT DOCUMENTS, change
"96724978", to read -- 9724978 --.

Signed and Sealed this

Eleventh Day of February, 2003

JAMES E. ROGAN
*Director of the United States Patent and Trademark Office*